US010286180B2

(12) United States Patent
Colbaugh

(10) Patent No.: US 10,286,180 B2
(45) Date of Patent: May 14, 2019

(54) SYSTEM AND METHOD FOR PROVIDING LIGHT THERAPY TO A SUBJECT USING TWO OR MORE WAVELENGTH BANDS OF ELECTROMAGNETIC RADIATION

(75) Inventor: Michael Edward Colbaugh, Level Green, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1874 days.

(21) Appl. No.: 13/696,450

(22) PCT Filed: Apr. 25, 2011

(86) PCT No.: PCT/IB2011/051788
§ 371 (c)(1),
(2), (4) Date: Nov. 6, 2012

(87) PCT Pub. No.: WO2011/141842
PCT Pub. Date: Nov. 17, 2011

(65) Prior Publication Data
US 2013/0053929 A1     Feb. 28, 2013

Related U.S. Application Data

(60) Provisional application No. 61/334,600, filed on May 14, 2010.

(51) Int. Cl.
*A61M 21/02* (2006.01)
*A61N 5/06* (2006.01)
*A61M 21/00* (2006.01)

(52) U.S. Cl.
CPC .......... *A61M 21/02* (2013.01); *A61N 5/0618* (2013.01); *A61M 2021/0044* (2013.01);
(Continued)

(58) Field of Classification Search
CPC ........ A61N 1/36078; A61N 2005/0648; A61N 5/0618; A61N 2005/0663;
(Continued)

(56) References Cited

U.S. PATENT DOCUMENTS 4,858,609 A    8/1989  Cole
5,545,192 A    8/1996  Czeisler et al.
(Continued)

FOREIGN PATENT DOCUMENTS

FR    2640512 A1    6/1990
JP     496764 A     3/1992
(Continued)

OTHER PUBLICATIONS

Roger J. Cole; "Bright-Light Mask Treatment of Delayed Sleep Phase Syndrome", Journal of Biological Rhythms, vol. 17, No. 1, Feb. 2002, pp. 89-101.
(Continued)

*Primary Examiner* — Amanda K Hulbert
*Assistant Examiner* — Natasha Patel

(57) ABSTRACT

Light therapy is provided to a subject through a sleep mask. The sleep mask is configured to deliver electromagnetic radiation to the closed eyelids of the subject within two separate wavelength bands. The first wavelength band is therapeutically impactful in adjusting the sleep cycle of the subject. The second wavelength band preconditions the subject for delivery of the electro-magnetic radiation in the first wavelength band, maintains the apparent brightness of the electromagnetic radiation throughout therapy, enables cooling within the sleep mask, enhances the power efficiency of the sleep mask, and/or provides other benefits. The first wavelength band and the second wavelength band are selected based on attenuation of electromagnetic radiation by the eyelid of the subject.

15 Claims, 6 Drawing Sheets

(52) U.S. Cl.
CPC .......... *A61N 2005/0648* (2013.01); *A61N 2005/0652* (2013.01); *A61N 2005/0663* (2013.01)

(58) Field of Classification Search
CPC .......... A61N 2005/0652; A61M 21/02; A61M 2021/0044
See application file for complete search history.

(56) References Cited

U.S. PATENT DOCUMENTS

| | | | |
|---|---|---|---|
| 6,350,275 B1 * | 2/2002 | Vreman | A61M 21/00 607/88 |
| 6,623,512 B1 | 9/2003 | Heller et al. | |
| 2004/0225340 A1 * | 11/2004 | Evans | A61M 21/00 607/88 |
| 2006/0136018 A1 * | 6/2006 | Lack | A61M 21/00 607/88 |
| 2006/0217690 A1 | 9/2006 | Bastin et al. | |
| 2008/0269849 A1 | 10/2008 | Lewis | |
| 2009/0018621 A1 | 1/2009 | Vogler et al. | |
| 2010/0174345 A1 * | 7/2010 | Ashdown | A61N 5/0618 607/88 |

FOREIGN PATENT DOCUMENTS

| | | |
|---|---|---|
| JP | 8257052 A | 10/1996 |
| JP | 2009266484 A | 11/2009 |
| WO | 2007116341 A1 | 10/2007 |
| WO | 2008146220 A2 | 12/2008 |
| WO | 2009023968 A1 | 2/2009 |
| WO | 2010044708 A1 | 4/2010 |
| WO | 2010076706 A1 | 7/2010 |
| WO | 2010076707 A1 | 7/2010 |
| WO | 2010076708 A1 | 7/2010 |
| WO | 2010076709 A1 | 7/2010 |
| WO | 2010076710 A1 | 7/2010 |
| WO | 2010122446 A1 | 10/2010 |

OTHER PUBLICATIONS

Latsuhisa Ando et al; "Light Attenuation by the Human Eyelid", Society Biological Psychiatry, 1996, vol. 39, pp. 22-25.
Mark S. Rea et al; "A Model of Phototransduction by the Human Circadian System", Brain Research Reviews, vol. 50, 2005, pp. 213-228.
Ludovic. Mure et al; "Melanopsin-Dependent Nonvisual Responses: Evidence for Photopigment Bistability in Vivo", Dept of Biology John Hopkins University, Baltimore, MA pp. 1-13.
David W. Rimmer et al; "Dynamic Resetting of the Human Circadian Pacemaker by Intermittent Bright Light", Am. J. Physiol Regulatory Integratice Comp Physiol, vol. 279, pp. 1574-1579, 2000.
Ando K. Kripke et al; "Light Mask 500 Lux Treatment for Delayed Sleep Phase Syndrome", Prog. Neuropsychopharmacol Biol Psychiatry, 1999, vol. 23, No. 1, pp. 15-24.
M.J. Moseley; "Light Transmission Through the Human Eyelid: In Vivo Measurement", Dept. of Ophthalmology, vol. 8, Apr. 1998.
Anthony N. Van Den Pol et al; "Circadian System of Mice Integrates Brief Light Stimuli", Am. J. Physiol Regul. Integr. Comp. Physiol, vol. 275, No. 2, pp. 654-657. Aug. 1998.
T. Hatonen et al; "Suppression of Melatonian by 2000-Lux Light in Humans With Closed Eyelids", Biol. Psychiatry, Sep. 15, 1999, vol. 46, No. 6, pp. 827-831.

* cited by examiner

SYSTEM AND METHOD FOR PROVIDING LIGHT THERAPY TO A SUBJECT USING TWO OR MORE WAVELENGTH BANDS OF ELECTROMAGNETIC RADIATION

The invention relates to the delivery of light therapy to a subject through eyelids of the subject using a sleep mask as the delivery mechanism.

The direction of radiation on a subject to impact the Circadian rhythms and/or to address disorders of the subject related to melatonin and/or serotonin levels in the subject are known. Generally, these treatments involve shining light directly towards a patient's eyes while the patient is awake to alleviate or cure light deficient disorders including Seasonal Affective Disorder (SAD), circadian sleep disorders and circadian disruptions associated with jet-lag, and shiftwork.

While some systems may be configured to administer phototherapy to a subject as the subject sleeps, these systems tend to only emit electromagnetic radiation in a single wavelength band.

One aspect of the invention relates to a sleep mask configured to provide light therapy to a subject. In one embodiment, the sleep mask comprises a shield, a first set of one or more radiation sources, a second set of one or more radiation sources, and a controller. The shield is configured to cover the eyes of a subject wearing the sleep mask such that the shield provides a barrier between ambient radiation and the eyes of the subject. The first set of one or more radiation sources is carried by the shield, and is configured to emit radiation in a first wavelength band onto the eyelid of the subject if the subject is wearing the sleep mask, wherein the first wavelength band includes wavelengths of electromagnetic radiation that impact the sleep cycle of the subject. The second set of one or more radiation sources is carried by the shield, and is configured to emit radiation in a second wavelength band onto the eyelid of the subject if the subject is wearing the sleep mask, wherein the second wavelength band includes wavelengths of electromagnetic radiation that precondition the non-visual system of the subject for reception of electromagnetic radiation in the first wavelength band. The controller is configured (i) to control emission of radiation by the first set of radiation sources such that the first set of radiation sources emit radiation in pulses, and (ii) to control emission of radiation by the second set of radiation sources such that the second set of radiation sources emit radiation between the pulses of radiation emitted by the first set of radiation sources that preconditions the non-visual system of the subject for reception of electromagnetic radiation in the first wavelength band during the pulses of radiation emitted by the first set of radiation sources.

Another aspect of the invention relates to a method of providing light therapy to a subject. In one embodiment, the method comprises emitting pulses of electromagnetic radiation in a first wavelength band onto the closed eyelid of the subject, wherein the first wavelength band includes wavelengths of electromagnetic radiation that impact the Sleep cycle of the subject; and emitting electromagnetic radiation in a second wavelength band onto the closed eyelid of the subject, wherein the second wavelength band includes wavelengths of electromagnetic radiation that precondition the non-visual system of the subject for reception of electromagnetic radiation in the first wavelength band, and wherein emission of electromagnetic radiation in the second wavelength band onto the closed eyelid of the subject preconditions the non-visual system of the subject for reception of electromagnetic radiation in the first wavelength band during the pulses of electromagnetic radiation in the first wavelength band.

Yet another aspect of the invention relates to a system configured to provide light therapy to a subject. In one embodiment, the system comprises means for emitting pulses of electromagnetic radiation in a first wavelength band onto the closed eyelid of the subject, wherein the first wavelength band includes wavelengths of electromagnetic radiation that impact the Sleep cycle of the subject; and means for emitting electromagnetic radiation in a second wavelength band onto the closed eyelid of the subject, wherein the second wavelength band includes wavelengths of electromagnetic radiation that precondition the non-visual system of the subject for reception of electromagnetic radiation in the first wavelength band, and wherein emission of electromagnetic radiation in the second wavelength band onto the closed eyelid of the subject preconditions the non-visual system of the subject for reception of electromagnetic radiation in the first wavelength band during the pulses of electromagnetic radiation in the first wavelength band.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 1:
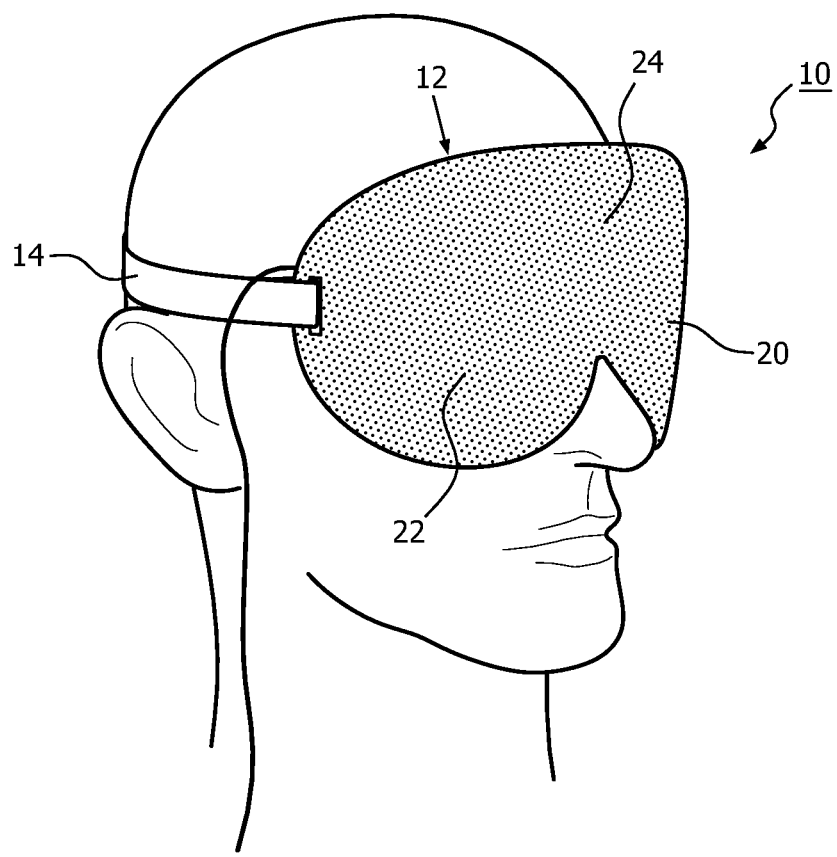
FIG. 1 illustrates a sleep mask, in accordance with one or more embodiments of the invention.
Figure 2:
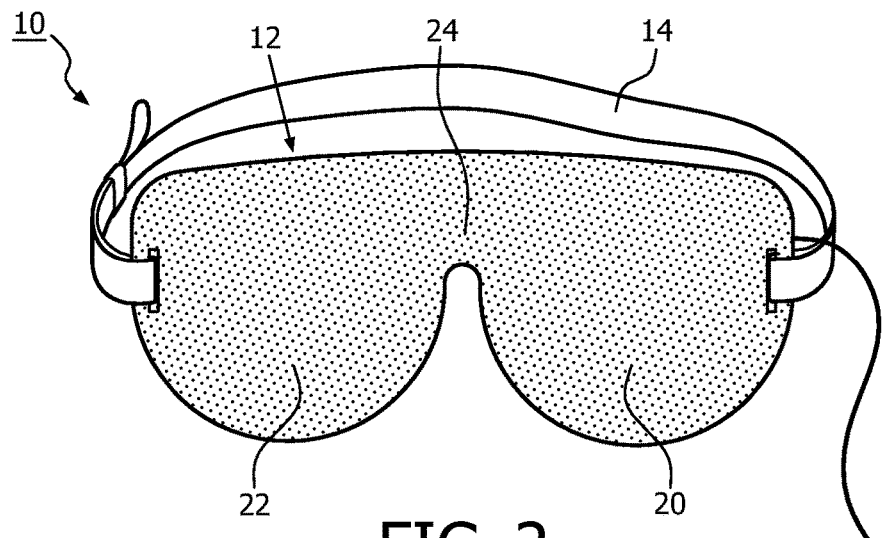
FIG. 2 illustrates a sleep mask, according to one or more embodiments of the invention.
Figure 3:
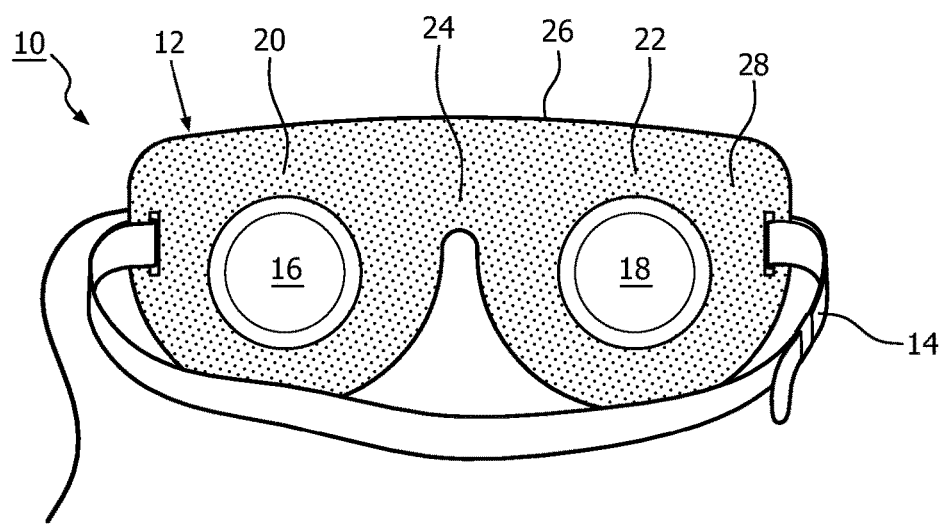
FIG. 3 illustrates a sleep mask, in accordance with one or more embodiments of the invention.

FIGS. 1-3 illustrate a sleep mask 10 configured to provide light therapy to a subject. Sleep mask 10 may provide a comfortable delivery mechanism for the light therapy, and may deliver the light therapy to the subject while the subject is asleep, in the process of going to sleep, and/or waking from sleep. In one embodiment, sleep mask 10 includes one or more of a shield 12, a strap 14, a first lighting module 16, and/or a second lighting module 18.

As can be seen in FIG. 1, shield 12 is configured to cover the eyes of the subject wearing sleep mask 10. In one embodiment, shield 12 includes a first shield portion 20 and a second shield portion 22. First shield portion 20 is configured to cover a first eye of the subject. Second shield portion 22 is configured to cover a second eye of the subject. In order to comfortably cover the first eye and the second eye of the subject, first shield portion 20 and second shield portion 22 are substantially larger than the ocular openings of the eyes of the subject.

In one embodiment, first shield portion 20 and second shield portion 22 are joined by a connecting shield portion 24. Connecting shield portion 24 is configured to rest on at least a portion of the nose of the subject (e.g., across the bridge of the nose) when the subject is wearing sleep mask 10. In some instances (not shown), connecting shield portion 24 may be narrower or thicker than the embodiment depicted in FIGS. 1-3.

In one embodiment, shield 12 is formed from flexible materials. The flexibility of shield 12 may enhance the comfort of shield 12 to the subject. The side of shield 12 visible in FIG. 3 faces toward the subject during use. On this side, a base surface 26 substantially impermeable to liquids may be formed. For example, the impermeable base surface 26 may be formed by a flexible plastic material such as polycarbonate, polyester, and/or other materials. The impermeability of base surface 26 may protect electronic components of sleep mask 10 carried within shield 12 from moisture.

In one embodiment, shield 12 includes a cushioning layer 28 disposed on base surface 26. Cushioning layer 28 is formed from a soft, resilient material. For example, cushioning layer 28 may be formed from foam, fabric, fabric/foam laminate, and/or other materials. During use, cushioning layer 28 provides the innermost surface to the subject, and engages the face of the subject. As such, the softness of cushioning layer 28 provides a cushion for the face of the subject, and enhances the comfort of sleep mask 10 to the subject.

As will be appreciated from the foregoing and FIGS. 1-3, during use shield 12 provides a barrier between ambient radiation and the eyes of the subject. In one embodiment, shield 12 is opaque, and blocks ambient radiation (at least within the visible spectrum), thereby shielding the eyes of the subject from ambient radiation.

Strap 14 is configured to hold shield 12 in place on the subject. In the embodiments shown in FIGS. 1-3, strap 14 is attached to each of first shield portion 20 and second shield portion 22, and wraps around the head of the subject to hold sleep mask 10 in place on the head of the subject. Strap 14 may be adjustable in length (e.g., to accommodate different sized heads). Strap 14 may be formed from a resilient material (e.g., elastic) that stretches to accommodate the head of the user and holds shield 12 in place. It should be appreciated that the inclusion of strap 14 in the embodiments of sleep mask 10 illustrated in FIGS. 1-3 is not intended to be limiting. Other mechanisms for holding shield 12 in place on the subject are contemplated. For example, a more elaborate headgear may be implemented, an adhesive surface may be applied to shield 12 that removably adheres to the skin of the subject to hold shield 12 in place, a rigid or flexible frame (e.g., eyeglasses), and/or other mechanisms for holding shield 12 in place may be implemented.

Referring now to FIG. 3, first lighting module 16 and second lighting module 18 are mounted to first shield portion 20 and second shield portion 22, respectively, on the side of shield 12 that faces toward the face of the subject during use. First lighting module 16 and second lighting module 18 are backlit, and are configured to emit radiation onto the face of the subject on and/or about the eyes of the subject. As is discussed below, the radiation emitted by first lighting module 16 and second lighting module 18 has a wavelength (or wavelengths) that have a therapeutic impact on the subject, when they are delivered in accordance with an effective light therapy plan.

The target of the light therapy plan are the intrinsically photosensitive Retinal Ganglion Cells. The intrinsically photosensitive Retinal Ganglion Cells are a type of nerve cell in the retina that do not participate directly in vision. Instead, the intrinsically photosensitive Retinal Ganglion Cells are non-image-forming, and provide a stable representation of ambient light intensity. As a result, the intrinsically photosensitive Retinal Ganglion Cells participate in at least three key areas: (1) they play a role in synchronizing circadian rhythms to the light/dark cycle by providing length of day, length of night, and night-to-day and day-to-night transitional information, (2) the contribute to the regulation of pupil size, and (3) they contribute to photic regulation of, and acute photic suppression of, release of the hormone melatonin. For convenience, within this disclosure, the term "sleep cycle" will be used to refer to the circadian rhythms, and/or the production, suppression, and/or release of melatonin for the subject.

Figure 4:
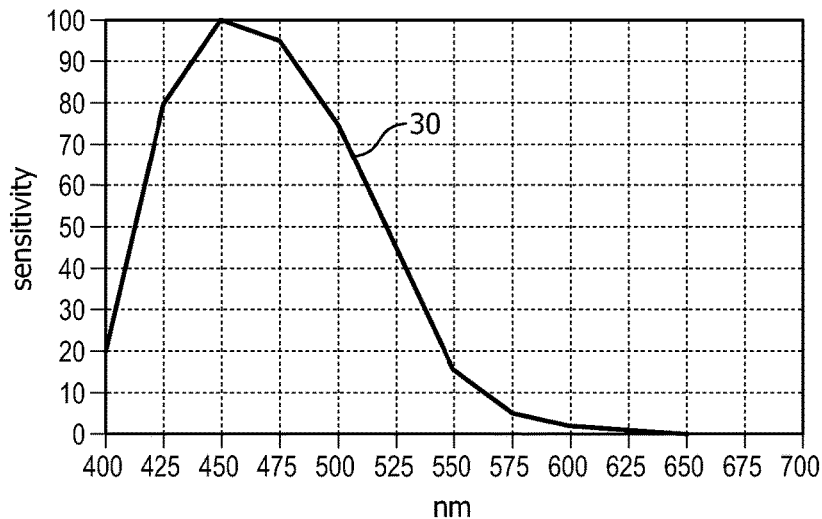
FIG. 4 illustrates a plot showing the response of intrinsically photosensitive Retinal Ganglion Cells versus wavelength.

FIG. 4 provides a plot 30 showing the response of intrinsically photosensitive Retinal Ganglion Cells versus wavelength. As can be seen in FIG. 4, the sensitivity of the intrinsically photosensitive Retinal Ganglion Cells peaks at approximately 450 nm, and drops off dramatically to an inflection point at approximately 550 nm. By virtue of this sensitivity profile, conventional light therapy systems and plans have focused on providing electromagnetic radiation to the eye of the subject between 450 nm and 475 nm. Particularly light therapy systems and plans in which electromagnetic radiation is provided directly to the open eye of the subject.

Figure 5:
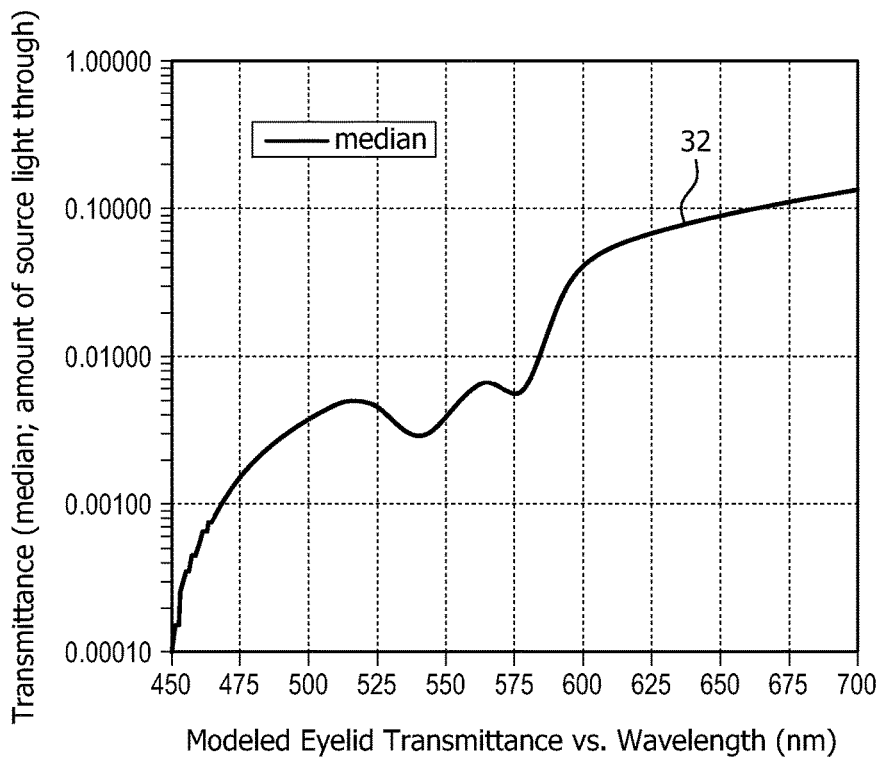
FIG. 5 illustrates a plot of transmittance of the human eye lid (on a logarithmic scale) versus wavelength.

FIG. 5 provides a plot 32 of transmittance of the human eye lid (on a logarithmic scale) versus wavelength. As can be seen in FIG. 5, transmittance through the eyelid varies somewhat dramatically based on wavelength. As such, although electromagnetic radiation at 450 nm may be the most efficient radiation for impacting intrinsically photosensitive Retinal Ganglion Cells to shift the sleep cycle when directing electromagnetic radiation to an open eye, attenuation of electromagnetic radiation at 450 nm may reduce the efficiency of this wavelength when electromagnetic radiation is being provided to the eye of the subject through the eyelid (e.g., as is done by the sleep mask 10 shown in FIGS. 1-3). As is shown in FIG. 5, light in the range of circadian modifying light in about the 450-550 nm range is attenuated by a factor of ten (10) or greater than longer wavelength light (e.g. wavelengths greater than 575 nm) as light passes through the eyelids.

Referring back to FIG. 3, in one embodiment, to enhance the efficiency of the light therapy provided to the subject, first lighting module 16 and second lighting module 18 are configured to emit electromagnetic radiation in a first wavelength band that is shifted to account for attenuation by the eyelid of the subject. For example, the first wavelength band may include wavelengths between about 475 nm and about 530 nm. In one embodiment, the first wavelength band is between about 490 nm and about 530 nm. In one embodiment, the first wavelength band is between about 500 and about 525 nm.

Figure 6:
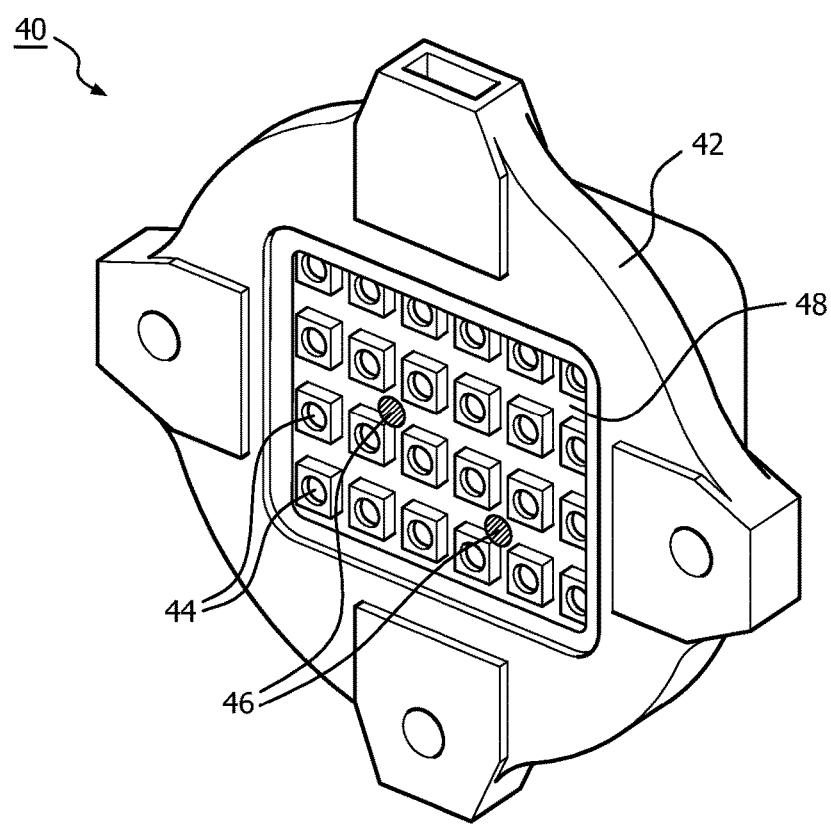
FIG. 6 illustrates a lighting module, in accordance with one or more embodiments of the invention.

FIG. 6 illustrates a lighting module 40. The lighting module 40 may be implemented in a sleep mask similar to or the same as sleep mask 10 (shown in FIGS. 1-3), and may serve as a first lighting module similar to or the same as first lighting module 16 and/or a second lighting module similar to or the same as second lighting module 18 (shown in FIGS. 1-3). The lighting module 40 may include one or more of a housing 42, a first set of one or more radiation sources 44, a second set of one or more radiation sources 46 and/or other components.

The housing 42 is configured to house and/or carry first set of radiation sources 44 and second set of radiation sources 46. The housing 42 is attachable (permanently or temporarily) to a sleep mask for use by the subject. As such, housing 42 may be formed from a rigid material, or housing 42 may be formed from a material with some resilient elasticity in order to provide comfort to the subject. As can be seen in FIG. 6, in one embodiment, housing 42 is configured to seat a substrate 48 carrying first set of radiation sources 44 and/or second set of radiation sources 46. Housing 42 may further be configured to carry an optical diffuser on the outside of first set of radiation sources 44 and/or second set of radiation sources 46. This will help to diffuse the electromagnetic radiation emitted by the sources 44 and/or 46, and provide electromagnetic radiation having a substantially uniform distribution onto the eyelid of the subject. This may enhance the comfort and/or usability of lighting module 40 during rest and/or sleep by the subject.

The first set of radiation sources 44 may be configured to emit electromagnetic radiation in the first wavelength band. The first set of radiation sources 44 are arranged in lighting module 40 such that if when lighting module 40 is installed in a sleep mask, the electromagnetic radiation emitted by first set of radiation sources 44 in the first wavelength band is directed onto the eyelid of the subject. Some of the electromagnetic radiation then passes through the eyelid and into the eye of the subject, where it impinges on the intrinsically photosensitive Retinal Ganglion Cells of the subject, and has a therapeutic impact on the sleep cycle of the subject (e.g., shifting the sleep cycle, prolonging the sleep period, etc.).

Conventional light therapy plans that provide electromagnetic radiation to the open eyes of the subject in a non-varying manner tend to become less effective over time. This is because the intrinsically photosensitive Retinal Ganglion Cells become de-sensitized to the electromagnetic radiation during prolonged, unbroken exposure. As a result, the impact of such electromagnetic radiation in altering the sleep cycle of the subject is reduced. To compensate for this effect in conventional, open eye light therapy, electromagnetic radiation at or near 450 nm may be provided to the open eye of the subject in a pulsed manner. The pulsation may have a regular, or irregular period, and the pulses may have a regular, or irregular, pulse length.

In order to further reduce de-sensitization of the intrinsically photosensitive Retinal Ganglion Cells to therapeutically effective electromagnetic radiation emitted by first set of radiation sources 44, second set of radiation sources 46 in lighting module 40 are configured to emit electromagnetic radiation in a second wavelength band that is different from the first wavelength band. For example, the second wavelength band may include electromagnetic radiation with a longer wavelength (e.g., yellow-green or red electromagnetic radiation) that is applied to the eye of the subject between pulses of the therapeutically effective electromagnetic radiation. The longer wavelength of the electromagnetic radiation in the second wavelength band may precondition the intrinsically photosensitive Retinal Ganglion Cells for the therapeutically effective electromagnetic radiation. In other words, the longer exposure to the longer wavelength light may reset the sensitivity of the intrinsically photosensitive Retinal Ganglion Cells to electromagnetic radiation in the first wavelength band. The preconditioning of the intrinsically photosensitive Retinal Ganglion Cells by the electromagnetic radiation in the second wavelength band may increase the frequency at which the electromagnetic radiation in the first wavelength band is therapeutically effective, may increase the duration for which pulses of electromagnetic radiation in the first wavelength band are effective for therapeutic purposes, and/or may increase the overall efficiency of the light therapy applied by lighting module 40 in regulating the sleep cycle of the subject in a therapeutic manner.

The electromagnetic radiation emitted by second set of radiation sources 46 may also be configured to maintain a level of apparent brightness of radiation between pulses. In a system like lighting module 40, which is designed to deliver electromagnetic radiation to the closed eyelid of the subject as the subject rests or sleeps, variation in apparent brightness of the electromagnetic radiation may be uncomfortable. Variation in color, on the other hand, may be less disruptive to the sleep and/or rest of the subject. Thus, the electromagnetic radiation delivered by second set of radiation sources 46 in the second wavelength band may not only enhance the efficiency of the light therapy, but may also (or instead) enhance the comfort and/or convenience of the therapy to the subject.

Returning briefly to FIGS. 4 and 5, it can be assessed from plots 30 and 32 that electromagnetic radiation that must pass through the eyelid of the subject will be most impactful between about 475 nm and about 530 nm. In one embodiment, light is used between about 490 nm and about 530 nm. In one embodiment, light is used between about 500 and about 525 nm. In fact, as discussed above, due to attenuation by the eyelid of the subject (and relative perception between wavelength ranges), electromagnetic radiation emitted outside the eyelid at about 600 nm with about 1/10 the intensity of electromagnetic radiation emitted outside the eyelid at about 500 nm will be perceived by the subject as having substantially the same apparent brightness.

Turning back to FIG. 6, in one embodiment, the second wavelength band includes electromagnetic radiation between 575 nm and 650 nm. In one embodiment, the second wavelength band includes electromagnetic radiation between about 530 nm and about 700 nm. In one embodiment, the second wavelength band includes electromagnetic radiation between about 590 nm and about 675 nm. In one embodiment, the second wavelength includes electromagnetic radiation between 590 nm and about 630 nm. In one embodiment, the second wavelength band includes electromagnetic radiation between about 600 nm and about 620 nm. As was discussed above with respect to FIG. 6, this means that the electromagnetic radiation emitted by second set of radiation sources 46 (in the second wavelength band) can be about 10 times less intense than electromagnetic radiation emitted by first set of radiation sources 44 (in the first wavelength band), and still maintain the same apparent brightness for the subject (with eyes closed). This reduced intensity for electromagnetic radiation emitted by second set of radiation sources 46 may provide energy savings within lighting module 40. The lower intensity requirements for electromagnetic radiation in the second wavelength band may enable second set of radiation sources 46 to less and/or less intense radiation sources than first set of radiation sources 44, as is shown in FIG. 6. The lower intensity at which electromagnetic radiation is emitted by second set of radiation sources 46 may further enable lighting module 40 (and/or components to which it is attached) to cool down between pulses of electromagnetic radiation emitted by first set of radiation sources 44. Thus, the selection of the second wavelength band in as described above may serve (1) to precondition the intrinsically photosensitive Retinal Ganglion Cells of the subject to the electromagnetic radiation in the first wavelength band, (2) maintain the apparent brightness of radiation to the subject between pulses of electromagnetic radiation in the first wavelength band, (3) provide enhanced power efficiency due to relatively high transmission through the eyelid, and/or (4) enable lighting module 40 to cool between pulses of electromagnetic radiation in the first wavelength band.

Figure 7:
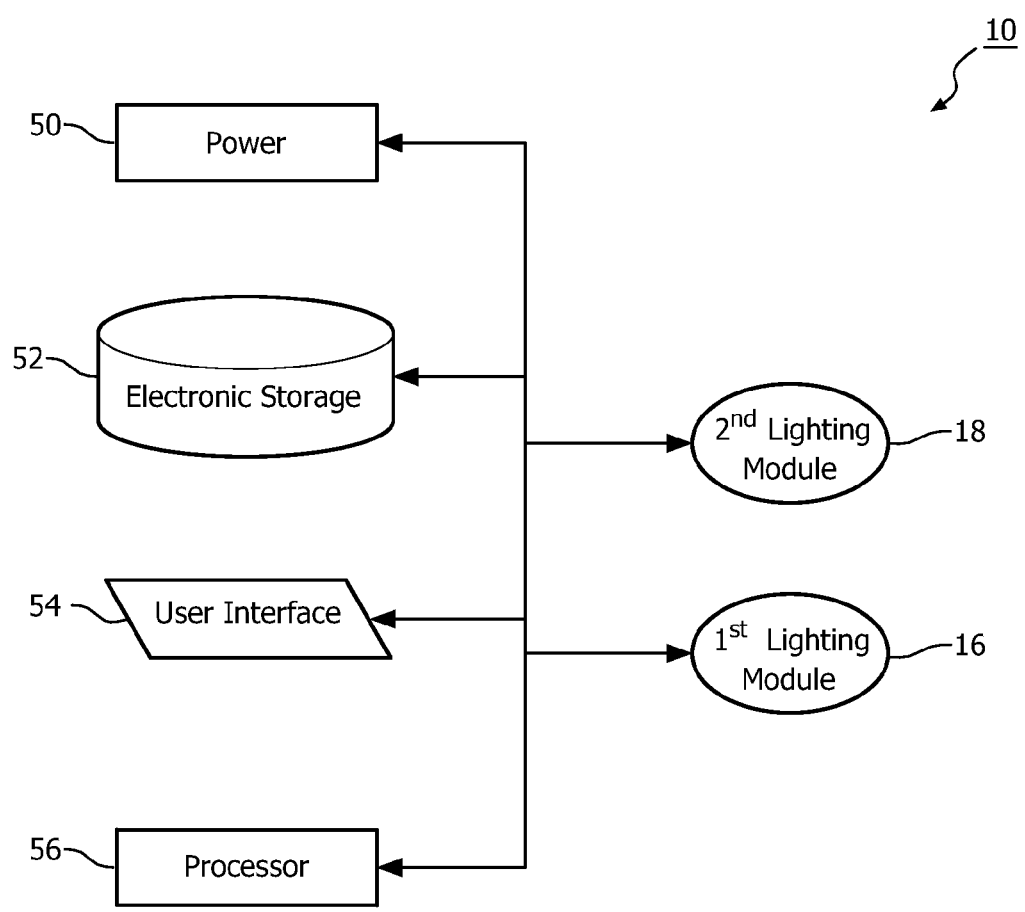
FIG. 7 is a schematic illustration of a sleep mask, according to one or more embodiments of the invention.

FIG. 7 is a schematic illustration of sleep mask 10, in accordance with one or more embodiments of the invention. As can be seen in FIG. 7, in addition to one or more of the components shown in FIGS. 1-3 and described above, sleep mask 10 may include one or both of a power source 50, electronic storage 52, a user interface 54, and/or a controller 56. In one embodiment, one or more of power source 50, user interface 54, and/or controller 56 are carried on shield 12 and/or strap 14 of sleep mask 10. In this embodiment, one or more of power source 50, electronic storage 52, user interface 54, and/or controller 56 may be removably attached to shield 12 and/or strap 14, and may be disconnectable from the rest of sleep mask 10. This will enable power source 50, electronic storage 52, user interface 54, and/or controller 56 to be removed from a given shield 12 and/or strap 14, and attached to another shield 12 and/or strap 14, which may be beneficial if shield 12 and/or strap 14 degrade over time and/or with usage and must be replaced. Similarly, in one embodiment, first lighting module 16 and second lighting module 18 are also removable/replaceable on shield 12. Power source 50, electronic storage 52, user interface 54, and/or controller 56 may control operation the radiation sources associated with first lighting module 16 and/or second lighting module 18, as is discussed below.

Power source 50 provides the power necessary to operate the radiation sources associated with first lighting module 16 and second lighting module 18, and/or to power electronic storage 52, user interface 54, and/or controller 56. Power source 42 may include a portable source of power (e.g., a battery, a fuel cell, etc.), and/or a non-portable source of power (e.g., a wall socket, a large generator, etc.). In one embodiment, power source 50 includes a portable power source that is rechargeable. In one embodiment, power source 50 includes both a portable and non-portable source of power, and the subject is able to select which source of power should be used to provide power to sleep mask 10.

In one embodiment, electronic storage 52 comprises electronic storage media that electronically stores information. The electronically storage media of electronic storage 52 may include one or both of system storage that is provided integrally (i.e., substantially non-removable) with sleep mask 10 and/or removable storage that is removably connectable to sleep mask 10 via, for example, a port (e.g., a USB port, a firewire port, etc.) or a drive (e.g., a disk drive, etc.). Electronic storage 44 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 52 may store software algorithms, information determined by controller 56, information received via user interface 54, and/or other information that enables sleep mask 10 to function properly. Electronic storage 52 may include media provided as a separate component within sleep mask 10. Electronic storage 52 may include media provided integrally with one or more other components of sleep mask 10 (e.g., controller 56).

User interface 54 is configured to provide an interface between sleep mask 10 and the subject (and/or a caregiver) through which the subject (and/or a caregiver) may provide information to and receive information from sleep mask 10. This enables data, results, and/or instructions and any other communicable items, collectively referred to as "information," to be communicated between the subject and controller 56. Examples of interface devices suitable for inclusion in user interface 54 include a keypad, buttons, switches, a keyboard, knobs, levers, a display screen, a touch screen, speakers, a microphone, an indicator light, an audible alarm, and a printer. In one embodiment, the functionality of which is discussed further below, user interface 54 actually includes a plurality of separate interfaces, including one interface that is carried on sleep mask 10, and a separate interface provided to view and/or manage stored information that has been retrieved from sleep mask 10 (e.g., provided by a host computer to which information from sleep mask 10 can be received).

It is to be understood that other communication techniques, either hard-wired or wireless, are also contemplated by the present invention as user interface 54. For example, the present invention contemplates that user interface 54 may be integrated with a removable storage interface provided by electronic storage 52. In this example, information may be loaded into sleep mask 10 from removable storage (e.g., a smart card, a flash drive, a removable disk, etc.) that enables the user(s) to customize the implementation of sleep mask 10. Other exemplary input devices and techniques adapted for use with sleep mask 10 as user interface 54 include, but are not limited to, an RS-232 port, RF link, an IR link, modem (telephone, cable or other). In short, any technique for communicating information with sleep mask 10 is contemplated by the present invention as user interface 54.

Controller 56 is configured to provide information processing and/or system control capabilities in sleep mask 10. As such, controller 56 may include one or more of a digital processor, an analog processor, a digital circuit designed to process information, an analog circuit designed to process information, a state machine, and/or other mechanisms for electronically processing information. In order to provide the functionality attributed to controller 56 herein, controller 56 may execute one or more modules. The one or more modules may be implemented in software; hardware; firmware; some combination of software, hardware, and/or firmware; and/or otherwise implemented. Although controller 56 is shown in FIG. 1 as a single entity, this is for illustrative purposes only. In some implementations, controller 48 may include a plurality of processing units. These processing units may be physically located within the same device (e.g., sleep mask 10), or controller 56 may represent processing functionality of a plurality of devices operating in coordination.

In one embodiment, controller 56 controls first lighting module 16 and second lighting module 18 in accordance with a predetermined light therapy algorithm. The predetermined light therapy algorithm may dictate the timing, the intensity, and/or the wavelength of the radiation emitted by first lighting module 16 and second lighting module 18 toward the face of the subject on or about the eyes of the subject. In one embodiment, the predetermined light therapy algorithm is stored in electronic storage 52, and is provided to controller 56 for execution via control of first lighting module 16 and second lighting module 18. In some instances, one or more aspects of the predetermined light therapy algorithm may be adjusted or customized for the subject. Adjustments and/or customizations to the predetermined light therapy algorithm may be input to sleep mask 10 via user interface 54. In one embodiment, electronic storage 52 stores a plurality of different predetermined light therapy algorithms, and the subject (and/or a caregiver) select the predetermined light therapy algorithm that is appropriate for the subject via user interface 46.

As was mentioned above, in one embodiment, the predetermined light therapy algorithm may dictate the timing of the administration of radiation to the subject by sleep mask 10. As such, in this embodiment, controller 56 includes a clock. The clock may be capable of monitoring elapsed time from a given event and/or of monitoring the time of day. The subject (and/or a caregiver) may be enabled to correct the time of day generated by the clock of controller 56 via, for example, user interface 54.

In one embodiment, first lighting module 16 and/or second lighting module 18 are configured to emit electromagnetic radiation in the first wavelength band and to emit electromagnetic radiation in the second wavelength band. Electromagnetic radiation in the first wavelength band is therapeutically effective in impacting the sleep cycles of the subject. Electromagnetic radiation in the second wavelength band preconditions the non-visual system of the subject (e.g., the intrinsically photosensitive Retinal Ganglion Cells) for reception of electromagnetic radiation in the first wavelength band. For example, first lighting module 16 and/or second lighting module 18 may individually include a first set of one or more radiation sources and a second set of one or more radiation sources similar to or the same as first set of radiation sources 44 and second set of radiation sources 46, respectively (shown in FIG. 6 and described above).

Figure 8:
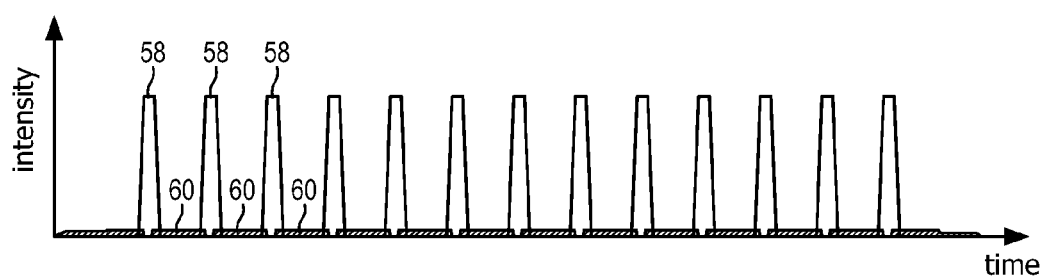
FIG. 8 illustrates a light therapy plan, in accordance with one or more embodiments of the invention.

In this embodiment, controller 56 is configured to control the timing and/or intensity of electromagnetic radiation in the first and second wavelength bands. The timing and/or intensity are controlled by controller 56 in accordance with a light therapy plan. By way of non-limiting example, FIG. 8 illustrates a light therapy plan that shows intensity of electromagnetic radiation as a function of time. The light therapy plan includes a plurality of pulses 58 of electromagnetic radiation in the first wavelength band, and emission of electromagnetic radiation in the second wavelength band during rest periods 60 between the pulses 58. For the reasons discussed above, the intensity of the emission of electromagnetic radiation in the second wavelength band during rest periods 60 is significantly lower than the intensity of electromagnetic radiation emitted in the first wavelength band during pulses 58. For example, the intensity of emitted electromagnetic radiation during pulses 58 may be about ten times greater than the intensity of electromagnetic radiation during rest periods 60. The duration of pulses 58 may be between 5 milliseconds and about 20 minutes In one embodiment, the duration of pulses 58 is between about 20 milliseconds and about 50 milliseconds. In one embodiment, the duration of pulses 58 is between about 2 minutes and about 20 minutes. The duration of rest periods 60 may be between about 30 seconds and about 90 minutes. In one embodiment, the duration of rest periods 60 is between about 30 seconds and about 1 minute. In one embodiment, the duration of rest periods 60 is between about 5 minutes and about 90 minutes.

Figure 9:
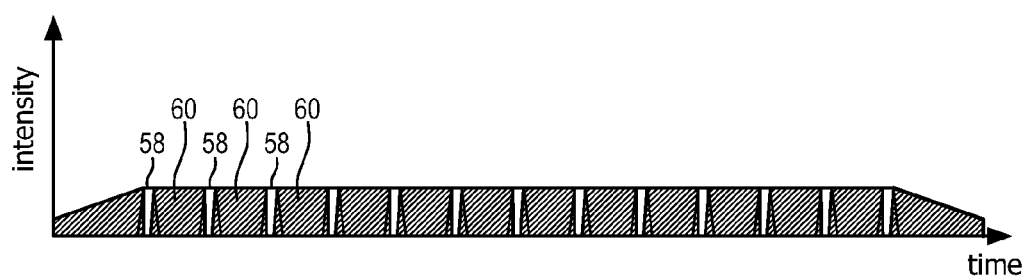
FIG. 9 illustrates perceived brightness of electromagnetic radiation received by a subject during a light therapy plan, according to one or more embodiments of the invention.

FIG. 9 illustrates the perception of electromagnetic radiation received by the subject during the light therapy plan illustrated in FIG. 8. Due to attenuation of electromagnetic radiation by the eyelid of the subject, the difference in intensity between the electromagnetic radiation emitted during pulses 58 and the electromagnetic radiation emitted during rest periods 60 is diminished and/or taken away completely. Depending on the selection the wavelength bands of light used for the first and second sources (there is variation across the spectrum of the cognitively perceived brightness of any given color, which effects the overall perception), the duration of the and intensity of the first light source (e.g. shorter faster-changing pulses are more visually disturbing), the second source intensity is designed to minimize the disturbance of a sleeper. In one embodiment, where the first wavelength band pulse 58 has rising or falling transitions greater than 5 seconds, the second light 60 is set according to attenuation differences in FIG. 5 plus the difference of perceived color brightness so that the two colors appear to be approximately the same brightness; as illustrated in FIG. 9. In another embodiment, where the rising or falling transitions of pulse 58 is less than 5 seconds, especially if they are substantially less than 1 second, then the second light 60 may be increased to an intensity greater (even multiple times) the eyelid attenuation corrected ratio of the first light's 58 intensity, in order to reduce the disturbing quality of a smaller or more quickly changing pulse 58. In this second embodiment the second light 60 must be bright enough to condition the visual system so that the disturbance caused by the quick first light 58 is effectively suppressed.

It will be appreciated that the illustration of the frequency, pulse duration, pulse shape, intensity, and other properties of the emission of electromagnetic radiation in the first and second wavelength bands during pulses 58 and/or rest periods 60 in FIG. 8 as being regular and/or uniform is not intended to be limiting. One or more of these and/or other properties may vary from pulse to pulse and/or from rest period to rest period. The variation may be part of a strategy to make the therapy more comfortable to the subject, and/or to increase the efficacy of the light therapy. By way of non-limiting example, intensity may be ramped up gradually over time, timing (e.g., pulse duration, rest period duration, period, etc.) may be randomized and/or varied to keep the subject from becoming accustomed to a given pattern, and/or other properties may be varied.

Returning to FIG. 6, in one embodiment, controller 56 is configured to control first lighting module 16 and/or second lighting module 18 such that the pulses of electromagnetic radiation delivered in the first wavelength band have a relatively high frequency (e.g., 10 times to once per minute) and relatively short pulses (e.g. 25 ms to 1 second). This technique may effect sleep cycle adjustment due in part to cone-receptor response in the eye (not just intrinsically photosensitive Retinal Ganglion Cells), and may include emitting short, repetitive flashes of electromagnetic radiation in the first wavelength range. In such an embodiment, the emission of electromagnetic radiation in the second wavelength band during rest periods between the pulses functions to maintain the apparent brightness of the system at a constant or relatively constant level. This may enhance the comfort for the subject, and may reduce instances in which the subject is awakened by the electromagnetic radiation. Further, in this embodiment, the cooling permitted by emitting electromagnetic radiation in the second wavelength band at a relatively low intensity (in comparison with the electromagnetic radiation emitted in the first wavelength band) may further enhance the comfort of the therapy for the subject, and/or reduce equipment malfunctions caused by overheating.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A sleep mask configured to provide light therapy to a subject, the sleep mask comprising:
    a shield configured to cover the eyes of a subject wearing the sleep mask such that the shield provides a barrier between ambient radiation and the eyes of the subject;
    a first set of one or more radiation sources carried by the shield, the first set of radiation sources being configured to emit radiation in a first wavelength band onto the eyelid of the subject if the subject is wearing the sleep mask, wherein the first wavelength band includes wavelengths of electromagnetic radiation that impact a sleep cycle of the subject after attenuation by the eyelid of the subject;
    a second set of one or more radiation sources carried by the shield, the second set of radiation sources being configured to emit radiation in a second wavelength band onto the eyelid of the subject if the subject is wearing the sleep mask, wherein the second wavelength band includes wavelengths of electromagnetic radiation that, after attenuation by the eyelid of the subject, precondition the non-visual system of the subject for reception of electromagnetic radiation in the first wavelength band; and
    a controller configured (i) to control emission of radiation by the first set of radiation sources such that the first set of radiation sources emit radiation in pulses, and (ii) to control emission of radiation by the second set of radiation sources such that the second set of radiation sources emit radiation between the pulses of radiation emitted by the first set of radiation sources that, after attenuation by the eyelid of the subject, preconditions the non-visual system of the subject for reception of electromagnetic radiation in the first wavelength band during the pulses of radiation emitted by the first set of radiation sources.

2. The sleep mask of claim 1, wherein the first set of radiation sources, the second set of radiation sources, and the controller are configured such that the intensity of the pulses of radiation in the first wavelength band emitted by the first set of radiation sources is at least about 10 times greater than the intensity of radiation in the second wavelength band emitted by the second set of radiation sources between the pulses of radiation emitted by the first set of radiation sources.

3. The sleep mask of claim 1, wherein the first set of radiation sources, the second set of radiation sources, and the controller are configured such that the apparent brightness of the radiation in the first wavelength band emitted by the first set of radiation sources after passing through the eyelid of the subject is substantially equal to the apparent brightness of the radiation in the second wavelength band emitted by the second set of radiation sources after passing through the eyelid of the subject.

4. The sleep mask of claim 1, wherein the first wavelength band is between about 475 nm and about 530 nm.

5. The sleep mask of claim 4, wherein the second wavelength band is between about 530 nm and about 700 nm.

6. A method of providing light therapy to a subject, the method comprising:
    emitting pulses of electromagnetic radiation in a first wavelength band onto the closed eyelid of the subject, wherein the first wavelength band includes wavelengths of electromagnetic radiation that impact a sleep cycle of the subject after attenuation by the eyelid of the subject; and
    emitting electromagnetic radiation in a second wavelength band onto the closed eyelid of the subject between the pulses of radiation emitted by the first set of radiation sources, wherein the second wavelength band includes wavelengths of electromagnetic radiation that, after attenuation by the eyelid of the subject, precondition the non-visual system of the subject for reception of electromagnetic radiation in the first wavelength band, and wherein emission of electromagnetic radiation in the second wavelength band onto the closed eyelid of the subject preconditions the non-visual system of the subject for reception of electromagnetic radiation in the first wavelength band during the pulses of electromagnetic radiation in the first wavelength band.

7. The method of claim 6, wherein the intensity of the pulses of electromagnetic radiation in the first wavelength band is at least about 10 times greater than the intensity of radiation in the second wavelength band emitted between the pulses of electromagnetic radiation in the first wavelength band.

8. The method of claim 6, wherein the apparent brightness of the radiation in the first wavelength band after passing through the eyelid of the subject is substantially equal to the apparent brightness of the radiation in the second wavelength band after passing through the eyelid of the subject.

9. The method of claim 6, wherein the first wavelength band is between about 475 nm and about 530 nm.

10. The method of claim 9, wherein the second wavelength band is between about 530 nm and about 700 nm.

11. A system configured to provide light therapy to a subject, the system comprising:
    means for emitting pulses of electromagnetic radiation in a first wavelength band onto the closed eyelid of the subject, wherein the first wavelength band includes wavelengths of electromagnetic radiation that impact a sleep cycle of the subject after attenuation by the eyelid of the subject; and
    means for emitting electromagnetic radiation in a second wavelength band onto the closed eyelid of the subject between the pulses of radiation emitted by the first set of radiation sources, wherein the second wavelength band includes wavelengths of electromagnetic radiation that, after attenuation by the eyelid of the subject, precondition the non-visual system of the subject for reception of electromagnetic radiation in the first wavelength band, and wherein emission of electromagnetic radiation in the second wavelength band onto the closed eyelid of the subject preconditions the non-visual system of the subject for reception of electromagnetic radiation in the first wavelength band during the pulses of electromagnetic radiation in the first wavelength band.

12. The system of claim 11, wherein the intensity of the pulses of electromagnetic radiation in the first wavelength band is at least about 10 times greater than the intensity of radiation in the second wavelength band emitted between the pulses of electromagnetic radiation in the first wavelength band.

13. The system of claim 11, wherein the apparent brightness of the radiation in the first wavelength band after passing through the eyelid of the subject is substantially equal to the apparent brightness of the radiation in the second wavelength band after passing through the eyelid of the subject.

14. The system of claim 11, wherein the first wavelength band is between about 475 nm and about 530 nm.

15. The system of claim 14, wherein the second wavelength band is between about 530 nm and about 700 nm.

* * * * *